United States Patent
Pasqualucci et al.

[11] Patent Number: 6,017,326
[45] Date of Patent: *Jan. 25, 2000

[54] SAFETY INTERLOCK SYSTEM FOR MEDICAL FLUID PUMPS

[75] Inventors: Joseph Pasqualucci; Frederick F. Schweitzer, both of Watertown, N.Y.

[73] Assignee: Sherwood Services, AG, Schaffhausen, Switzerland

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/006,081

[22] Filed: Jan. 19, 1993

Related U.S. Application Data

[63] Continuation of application No. 07/713,554, Jun. 7, 1991, Pat. No. 5,201,711, which is a continuation of application No. 07/442,030, Nov. 28, 1989, abandoned, which is a continuation of application No. 07/103,432, Sep. 30, 1987, Pat. No. 4,913,703.

[51] Int. Cl.[7] ................................................ A61M 1/00
[52] U.S. Cl. .................................... 604/153; 604/151
[58] Field of Search ............................ 604/30, 49, 67, 604/151, 152, 153, 150; 417/63, 360, 474–477

[56] References Cited

U.S. PATENT DOCUMENTS

| | | |
|---|---|---|
| 3,496,878 | 2/1970 | Hargest et al. . |
| 3,620,650 | 11/1971 | Shaw . |
| 3,739,943 | 6/1973 | Wilhelmson et al. . |
| 3,935,876 | 2/1976 | Massie et al. . |
| 4,080,967 | 3/1978 | O'Leary . |
| 4,137,913 | 2/1979 | Georgi . |
| 4,184,185 | 1/1980 | Casson et al. . |
| 4,184,815 | 1/1980 | Casson et al. . |
| 4,187,057 | 2/1980 | Xanthopoulos . |
| 4,210,138 | 7/1980 | Jess et al. . |
| 4,211,519 | 7/1980 | Hogan . |
| 4,221,543 | 9/1980 | Cosentino et al. . |
| 4,278,085 | 7/1981 | Shim . |
| 4,312,341 | 1/1982 | Zissimopoulos et al. . |
| 4,349,814 | 9/1982 | Akehurst . |
| 4,363,609 | 12/1982 | Cosentino et al. . |
| 4,373,525 | 2/1983 | Kobayashi . |
| 4,394,862 | 7/1983 | Shim . |
| 4,398,542 | 8/1983 | Cunningham . |
| 4,452,599 | 6/1984 | Albisser et al. . |
| 4,456,009 | 6/1984 | Vcelka et al. . |
| 4,460,358 | 7/1984 | Somerville et al. . |
| 4,464,172 | 8/1984 | Lichteenstein . |
| 4,492,531 | 1/1985 | Kenji et al. . |
| 4,493,706 | 1/1985 | Borsanyi et al. . |
| 4,515,535 | 5/1985 | D'Silva . |
| 4,515,584 | 5/1985 | Abe et al. . |
| 4,519,792 | 5/1985 | Dawe . |
| 4,540,964 | 9/1985 | Bleeke . |
| 4,543,458 | 9/1985 | Holce et al. . |
| 4,544,903 | 10/1985 | Grant . |
| 4,551,134 | 11/1985 | Slavik et al. . |
| 4,557,725 | 12/1985 | Heyne et al. . |
| 4,563,179 | 1/1986 | Sakai . |
| 4,565,500 | 1/1986 | Jeensalute et al. . |
| 4,568,254 | 2/1986 | Terada et al. . |

(List continued on next page.)

OTHER PUBLICATIONS

Kangaroo 300 Feeding Pump Operating Manual, pp. 1–12, Copyright 1983.

*Primary Examiner*—Gary Jackson
*Assistant Examiner*—William W. Lewis
*Attorney, Agent, or Firm*—Mark S. Leonardo; Brown, Rudnick, Freed & Gesmer, P.C.

[57] ABSTRACT

A medical fluid delivery set is provided with a magnetic field source in the region of its mounting to a fluid flow control apparatus. The flow control apparatus includes a magnetic field sensitive switching component which detects the proper placement of the delivery set on the flow control apparatus and prevents operation of the fluid delivery system unless a set is in proper position.

17 Claims, 4 Drawing Sheets

U.S. PATENT DOCUMENTS

| | | |
|---|---|---|
| 4,585,399 | 4/1986 | Baier . |
| 4,585,441 | 4/1986 | Archibald . |
| 4,599,055 | 7/1986 | Dykstra . |
| 4,601,211 | 7/1986 | Whistler . |
| 4,610,658 | 9/1986 | Buchwald et al. . |
| 4,623,331 | 11/1986 | Cewers et al. . |
| 4,636,144 | 1/1987 | Abe et al. . |
| 4,638,278 | 1/1987 | Bullock . |
| 4,650,469 | 3/1987 | Berg et al. . |
| 4,650,471 | 3/1987 | Tamari . |
| 4,652,260 | 3/1987 | Fenton, Jr. et al. . |
| 4,652,262 | 3/1987 | Veracchi . |
| 4,657,486 | 4/1987 | Stempfle et al. . |
| 4,661,093 | 4/1987 | Beck et al. . |
| 4,668,216 | 5/1987 | Martin et al. . |
| 4,673,389 | 6/1987 | Archibald et al. . |
| 4,685,902 | 8/1987 | Edwards et al. . |
| 4,688,595 | 8/1987 | Srebnik et al. . |
| 4,695,271 | 9/1987 | Goethel . |
| 4,702,675 | 10/1987 | Aldrovandi et al. . |
| 4,714,463 | 12/1987 | Archibald et al. . |
| 4,720,249 | 1/1988 | Krebs et al. . |
| 4,741,736 | 5/1988 | Brown . |
| 4,752,289 | 6/1988 | Balding et al. . |
| 4,755,109 | 7/1988 | Botts . |
| 4,758,228 | 7/1988 | Williams . |
| 4,798,580 | 1/1989 | DeMeo et al. . |
| 4,798,589 | 1/1989 | Tseo . |
| 4,798,590 | 1/1989 | O'Leary . |
| 4,808,089 | 2/1989 | Bucholtz et al. . |
| 4,838,860 | 6/1989 | Groshong et al. . |
| 5,694,782 | 12/1997 | Alsenz . |

SAFETY INTERLOCK SYSTEM FOR MEDICAL FLUID PUMPS

This is a continuation of application Ser. No. 7,713,554 filed on Jun. 7, 1991, now U.S. Pat. No. 5,201,711 which is a continuation of 07/442,030 filed on Nov. 28, 1989, now abandoned which is a continuation of 07/103/432 filed on Sep. 30, 1987, now U.S. Pat. No. 4,913,703.

BACKGROUND OF THE INVENTION

This invention relates to fluid delivery systems for providing perenteral nutrition, enternal nutrition or other fluids to patients who require infusion of fluids. The invention is particularly related to improvements in such systems which use a disposable fluid delivery set in conjunction with a fluid flow control unit, such as a pump motor set, for supplying such fluids to a patient at a controlled delivery rate.

The assignee of the present invention presently markets an enternal delivery system under the trade name "Kangaroo". The system includes a fluid delivery motor set and a disposable fluid delivery set, which includes a fluid tube, a drip chamber which is arranged to be mounted to recess on the motor set, a mounting member, also arranged to be mounted to a recess on the motor set, an outlet tube connected to the mounting member and a pump tube which connects the drip chamber to the mounting member and engages a motor driven rotor on the motor set to form a peristaltic pump.

In the Kangaroo enteral delivery system the engagement of the pump tube to the rotor controls the flow of fluid to the patient according to the speed of the rotor. In the event the delivery set is not properly mounted to the motor set and the pump tube is not firmly engaged with the rotor, an excess flow of fluid through the set can occur under force of gravity. Improper mounting of the drip chamber is unlikely because of the mechanical configuration of that component and its corresponding recess. Improper placement of the mounting member, e.g. below, above or outside of the receiving recess, is possible if the delivery set is installed on the motor set by an operator who has not received proper instruction in the operation of the system. Instances of such improper installation have been reported.

It is an object of the present invention to provide an interlock system which prevents operation of a fluid delivery system unless the delivery set is properly placed and installed on the flow control unit.

SUMMARY OF THE INVENTION

The present invention is applicable in a medical fluid delivery system which includes a fluid delivery set arranged to be mounted on a corresponding fluid delivery flow control apparatus. According to the invention there is provided a method for preventing improper system operation which comprises the steps of providing a switching component on the flow control apparatus which has a first electrical state when the delivery set is properly mounted to the flow control apparatus and a second electrical state when the delivery set is not properly mounted to the flow control apparatus. According to the invention operation of the flow control apparatus is enabled in response to the first electrical state and disabled in response to the second electrical state. The second electrical state will also cause an alarm to be activated when operation is attempted.

According to the invention there is provided a fluid flow control apparatus which is arranged to receive a corresponding fluid delivery set. The fluid flow control apparatus is provided with switching component responsive to proper mounting of a fluid delivery set and is provided with control means responsive to the switching component for permitting operation of the flow control apparatus only when the switching component detects proper mounting of the fluid delivery set. Preferably the switching component is a magnetic field sensitive component.

According to the present invention, there is provided a fluid flow control apparatus for a medical fluid delivery set, the improvement wherein the flow control apparatus is provided with a switching component responsive to proper mounting of said fluid delivery set and wherein there is provided control means in the flow control apparatus responsive to the switching component for permitting cooperation of said flow control apparatus only when said switching component detects proper mounting of the fluid delivery set According to the present invention, there is also provided a medical fluid delivery system including a fluid delivery set arranged to be mounted on a corresponding fluid delivery flow control apparatus, a method for preventing improper system operation comprising providing a switching component on the flow control apparatus arranged to have a first electrical state when the delivery set is properly mounted to the flow control apparatus and a second electrical state when said delivery set is not properly mounted to the flow control apparatus, enabling operation of said flow control apparatus in response to the first electrical state and disabling operation of the flow control apparatus and activating an alarm in response to the second electrical state.

According to the present invention, there is also provided a medical fluid delivery flow control apparatus adapted to be operatively connected to a conduit of a medical fluid delivery set for delivery of the medical fluid, the improvement comprising means responsive to improper operative connection of the conduit for interrupting operation of said flow control apparatus.

According to the present invention, there is also provided a disposable medical fluid delivery set including flexible tubing adapted to be operatively connected to a medical fluid delivery flow control apparatus for delivery of a medical fluid, the flow control apparatus including a switch means for interrupting the operation thereof, the improvement wherein the tubing includes switch activating means for activating the switch means upon improper operative connection of said tubing to the flow control apparatus.

According to the present invention, there is also provided a disposable medical fluid delivery set including flexible tubing adapted to be operatively connected to a medical fluid delivery flow control apparatus for delivery of a medical fluid, the flow control apparatus including a switch means for interrupting the operation thereof, the improvement wherein the tubing includes switch activating means for activating the switch means to permit pump operation only upon proper operative connection of the tubing to the flow control apparatus.

According to the present invention, there is also provided a medical fluid delivery peristaltic pump including a pump rotor adapted to be operatively connected to a conduit of a medical fluid delivery set for delivery of medical fluid to a means for delivery of the medical fluid to a patient, the improvement comprising switch means responsive to improper operative connection of the conduit with the pump rotor for interrupting rotation of the rotor.

In accordance with the invention there is provided a disposable medical fluid delivery set arranged to be mounted to a fluid flow control apparatus which is arranged for operating with portions of the set for controlling the rate of fluid delivery. According to the invention there is provided an improvement comprising a magnetic field source on the fluid delivery set, the source being arranged in a position on the set which corresponds to a magnetic field sensitive component on the control apparatus. In a preferred embodiment the fluid delivery set includes at least one mounting member arranged for attachment to a corresponding receiving member on the control apparatus and the magnetic field source is mounted on the mounting member.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
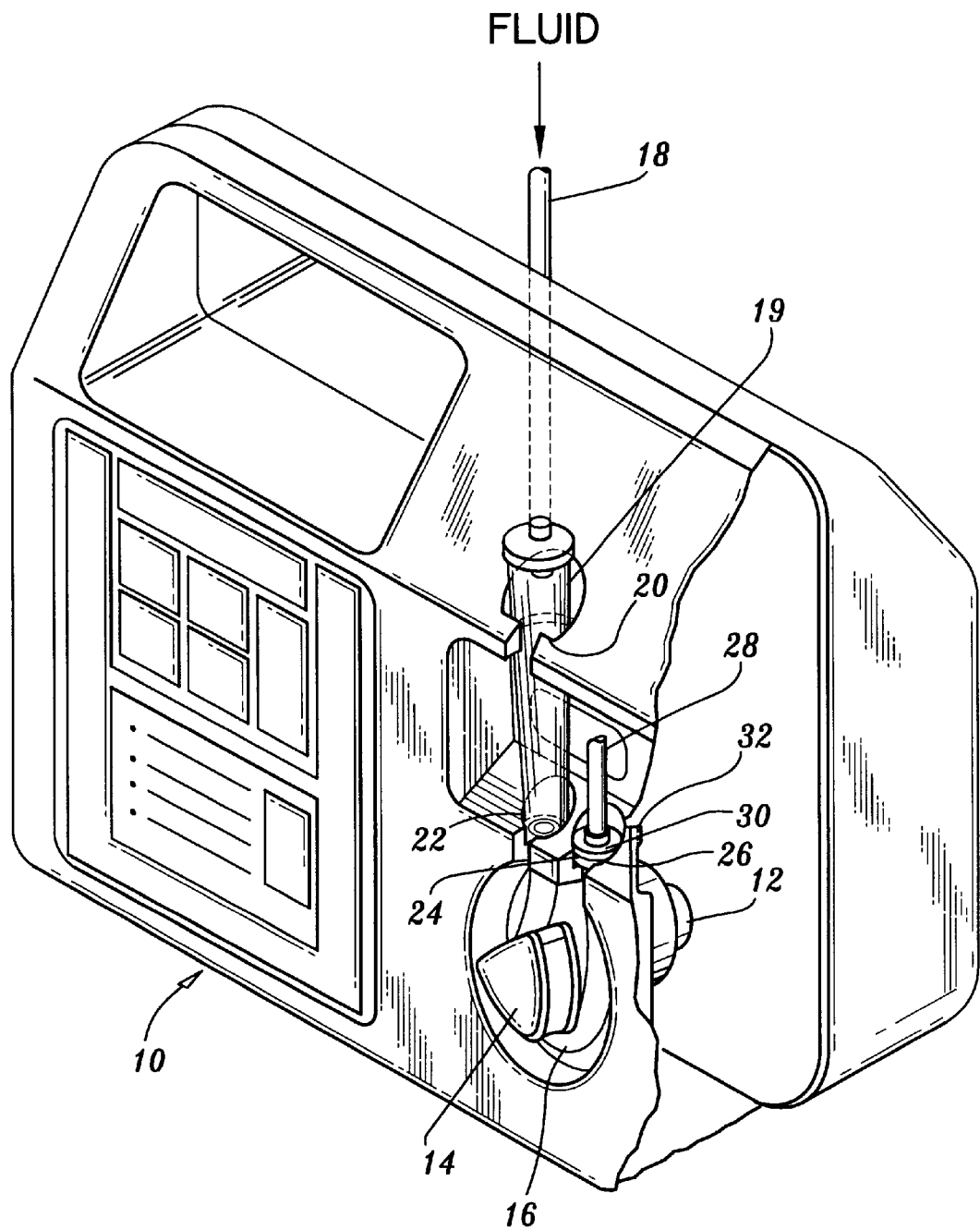
FIG. 1 a perspective view of a medical fluid delivery system incorporating the present invention.

FIG. 1 is a perspective view of an enteral fluid delivery system incorporating the present invention. The system includes a motor set 10 upon which is mounted a disposable delivery set which includes inlet tube 18 which is connected to a source of fluid, drip chamber 19 which is connected to receive fluid from tube 18 and is mounted in recesses 20 and 22 on motor set 10. The delivery set also includes a pump tube 16 which is connected to the bottom of drip chamber 9 and which surrounds a pump rotor 14 on motor set 10 to form a peristaltic pump. The delivery set also includes a circular mounting member 24 which is received in mounting recess 26 and which connects pump tube 16 to outlet tube 28. Rotor 14 on motor set 10 is driven by motor 12 and rotates at various speeds to control the rate of delivery of fluid, such as enteral nutrition fluid, to a patient.

Those familiar with the art will recognize that similar delivery sets and motor sets are used in connection with delivery of other medical fluids, such as intravenous i.e. perenteral fluids, or blood. In some systems rather than provide a motor driven pump, as the motor set 10 of FIG. 1, there is provided a flow control apparatus which controls the flow of fluid by gravity, for example by exerting a value-like force on a portion of the fluid delivery set.

The present invention is concerned with assuring proper placement of the fluid delivery set onto the motor set or other flow control apparatus, and in particular with the proper placement of the pump tube 16 around the rotor 14 to form a peristaltic pump which provides accurate and controlled delivery rates.

Figure 3A:
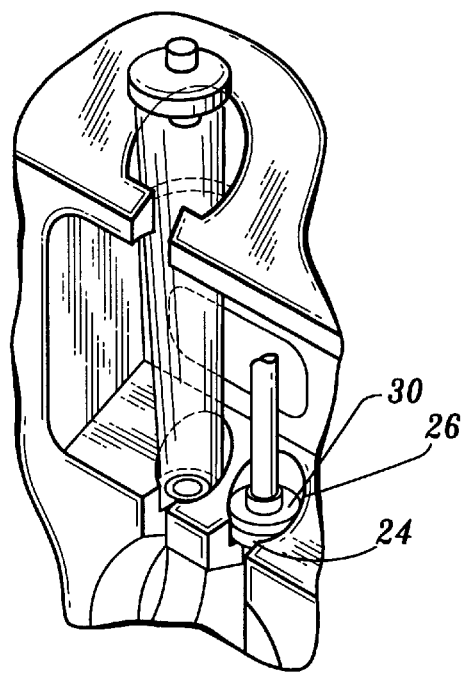
FIGS. 3A, 3B, 3C and 3D are detailed illustrations of a portion of the FIG. 1 system illustrating correct and incorrect positioning of a fluid delivery set.
Figure 3B:
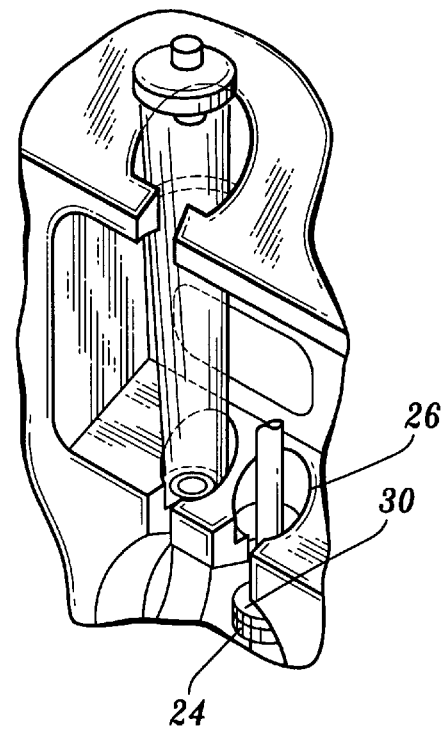
Figure 3C:
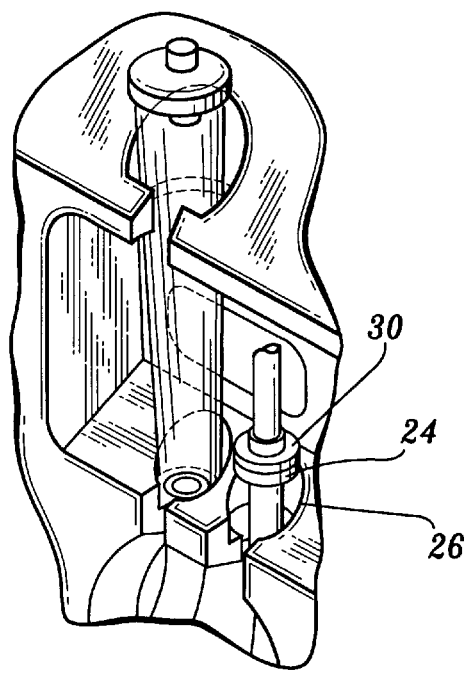
Figure 3D:
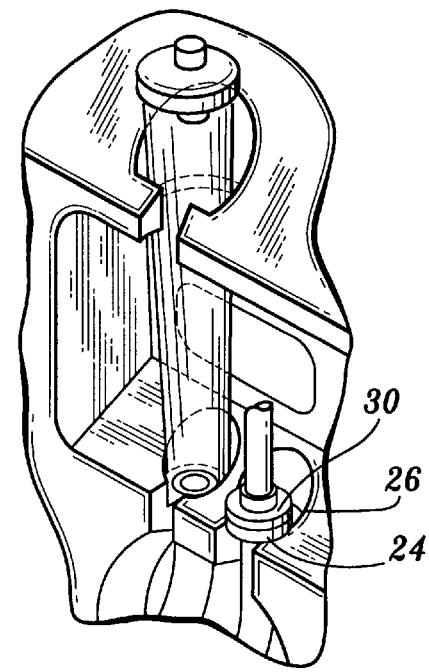

Pump tube 16 is mounted to drip chamber 19 at its inlet and (22) and mounted to mounting member 24 at its outlet end. As illustrated in FIG. 1, drip chamber 19 is received in recesses 20 and 22 on motor set 10 and mounting member 24 is received in recess 26. When properly mounted pump tube 16, which is typically silicone tubing is tightly stretched around rotor 14 so that the points of rotor contact on tube 16 close the passage of fluid. Referring to FIG. 3 there is shown in FIG. 3A the correct arrangement of the drip chamber and mounting member in the recesses on motor set 10. As shown in FIG. 3A mounting member 24 should be fully received into recess 26. It has come to the inventors' attention that in some cases the mounting member 24 may be improperly installed by inexperienced personnel so that mounting member 24 is seated below recess 26 as shown in FIG. 3B. This arrangement can be hazardous to a patient because of excess and uncontrolled flow of fluid through the delivery set under force of gravity, whereby fluid is delivered at a higher rate than properly specified. Another improper mounting of the delivery set is illustrated in FIG. 3C, wherein mounting member 24 is caught on the lip of recess 26 and not properly seated in the recess itself. Another improper mounting is shown in FIG. 3D wherein mounting member 24 is not placed completely back into recess 26, but seats on the outer edge thereof.

In accordance with the present invention an arrangement is provided for detecting the proper placement of mounting member 24 in recess 26. Improper placement of drip chamber 19 is unlikely since it must engage both recess 20 and recess 22.

Figure 2:
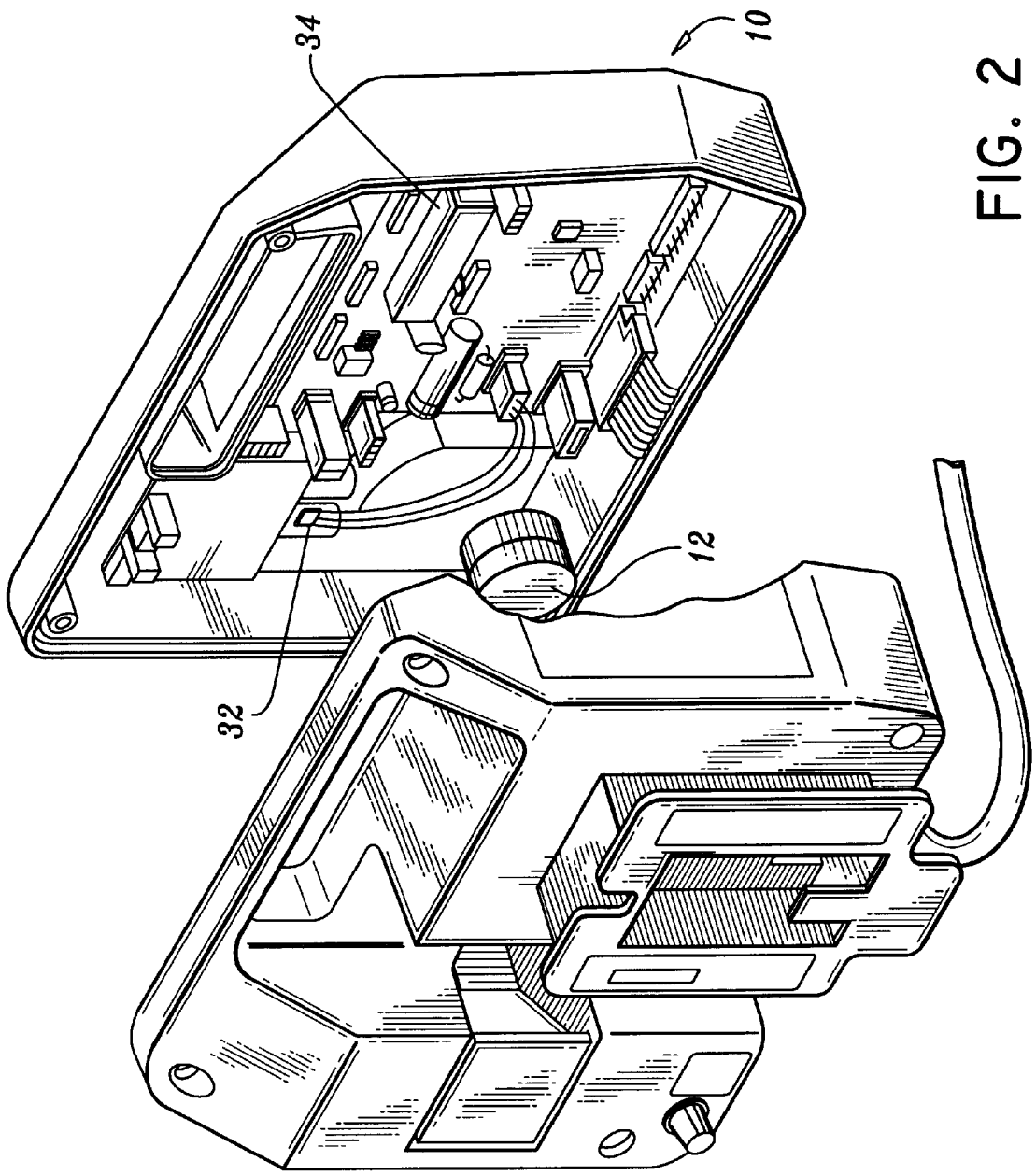
FIG. 2 is a perspective view of the interior of the medical fluid delivery system of FIG. 1.

In order to detect the proper placement of mounting member 24 in recess 26 there is provided a magnetic field source 30 which is a toroidal shaped piece added to mounting member 24 and surrounding the fluid passage thereof. A magnetic field detector 32 is provided within the motor set 10 and arranged to detect the magnetic field from magnetic field source 30 when mounting member 24 is properly received into recess 26. FIGS. 1 and 2 shown generally the internal arrangement of motor set 10 indicating the placement of magnetic field detector 32 against the inside wall of the motor set adjacent recess 26.

Figure 4:
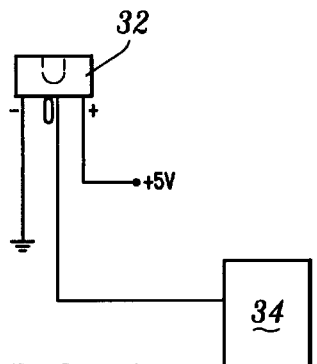
FIG. 4 is a schematic diagram illustrating the electrical connection of a switching component in the fluid delivery system of FIG. 1.

Magnetic field detector 32 is preferably a magneto resistive switching element, such as part No. SS21PE, available from Microswitch of Freeport, Ill. When connected as shown in FIG. 4 this part provides an output of plus 5 volts when not in the presence of a magnetic field and zero volts when in the presence of either polarity of magnetic field. The zero or plus 5 volt output signal of switching element 32 is connected to microprocessor 34 as a digital input signal to cause the motor set 10 to provide an error signal if an operator attempts to operate the motor set with an improperly placed delivery set. The error signal prevents operation of the motor set and preferably causes an alarm signal to be provided.

Figure 5:
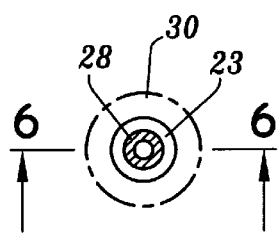
FIG. 5 is a top view of a mounting member in accordance with the present invention.
Figure 6:
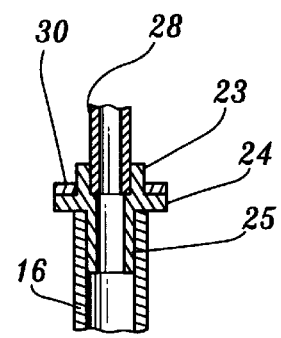
FIG. 6 is a cross-sectional view of a mounting member taken along the lines illustrated in FIG. 5.

FIG. 5 is a top view of mounting member 24 which is circular in cross-section and includes a central passage for fluids. A magnetic source 30 which is toroidal in shape is attached directly to the shoulder of mounting member 24 as shown in the cross-sectional view of FIG. 6. Magnetic source 30 surrounds an upwardly projecting tube receiving member 23 which connects to outlet tube 28. Mounting member 24 also includes a downwardly attending tube engaging member 25 which receives peristaltic pump tube 16. As an alternate to providing a separate magnetic field source 30, mounting member 24 can be formed entirely from magnetic material.

Figure 7:
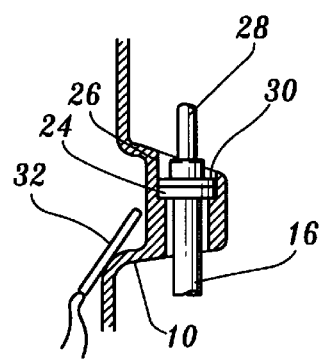
FIG. 7 is a cross-sectional view of the FIG. 1 fluid delivery system showing details of the components of the present invention.
Figures 8, 9:
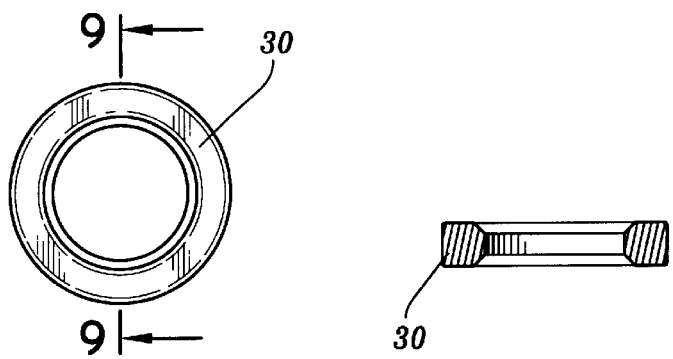
FIG. 8 is a plan view of a magnetic field source used in the fluid delivery system of FIG. 1.
FIG. 9 is a cross-sectional view of a magnetic field source taken along the lines illustrated in FIG. 8.

FIG. 7 shows the details of one arrangement for detecting the presence of the magnetic element 30 surrounding mounting member 24. The magnetic sensitive switching component 32 is arranged on the inside wall of the motor set 10 with its magneto sensitive and pointing at an angle of 42.5© toward the magnetic field source 30 mounted on mounting member 24. The end of magnetic sensitive switching element 32 is vertically spaced 0.210 inches from the top of magnetic field source 30 and is horizontally spaced 0.075 inches from the outside diameter of magnetic field source 30. Details of magnetic field source 30 showing mechanical dimensions are illustrated in FIGS. 8 and 9.

While it is believed that a wide variety of magnetic materials are suitable for the magnetic field source, the inventors have found that a material composed of 88% stronium ferrite and 12% #6 nylon to be a suitable material. This material is available from Tengan of Ostsego, Mich. The material is magnetized in the axial direction to a magnetic strength of 400 to 500 gauss at the surface edge.

Those skilled in the art will recognize that while the invention has been described with reference to application on an enteral delivery system, the present invention is likewise useable in connection with detecting the proper placement of a disposable delivery set on other medical fluid delivery systems, such as intravenous pumps or blood infusion pumps.

While the present invention has been described with respect to an embodiment which uses a magnetic field source on the disposable delivery set and a magnetic field sensitive switching element on the motor set, those skilled in the art will recognize that other arrangements for detecting the presence of and proper placement of a mounting member on the motor set are possible, including arrangements of mechanical micro-switches on a pump motor set and switch activating devices on the disposable delivery set.

While there has been described what is believed to be the preferred embodiment of the invention, those skilled in the art will recognize that other and further modifications may be made thereto without departing from the spirit of the invention, and it is intended to claim all such changes and modifications as fall within the true scope of the invention.

We claim:

1. A medical fluid delivery flow control apparatus including a flow control member thereon adapted to be operatively connected to a conduit of a medical fluid delivery set for controlled delivery of the medical fluid therethrough to a patient, the improvement comprising a magnetic sensor on a flow control apparatus responsive to operative connection of a portion of the conduit in predetermined alignment of a portion of said delivery set in relation to said sensor for enabling operation of said flow control member in response to proper operative connection of said conduit on said flow control apparatus, wherein said predetermined alignment of said portion of said fluid delivery set corresponds to a predetermined alignment of said conduit about said flow control member.

2. A medical fluid delivery system including medical fluid delivery set having flexible tubing adapted to be operatively connected to a medical fluid delivery flow control apparatus for delivery of a medical fluid therethrough, the fluid delivery system comprising a flow control apparatus including a switch for interrupting the operation thereof and a flow control member, a medical fluid delivery set including a switch actuating means thereon for actuating said switch on said flow control apparatus upon proper operative connection of said actuating means in a predetermined and spaced apart relationship with said switch and in response to proper operative connection of a portion of said fluid delivery set in relation to said switch to enable operation of said flow control member, wherein said predetermined alignment of said portion of said fluid delivery set corresponds to a predetermined alignment of said conduit about said flow control member.

3. A medical fluid delivery system comprising:

a peristaltic pump including a flow control member thereon and a corresponding fluid delivery set operatively mountable on said peristaltic pump, a controller on said peristaltic pump for enabling operation of said flow control member on said peristaltic pump, said control means including a sensor for detecting a predetermined and spaced apart alignment of a portion of said fluid delivery set generally adjacent to said sensor on said peristaltic pump, and said controller enabling the operation of said peristaltic pump in response to the detection of said portion of said fluid delivery set in the predetermined and spaced apart alignment on said peristaltic pump by said sensor and the proper operative mounting of said fluid delivery set about said flow control member.

4. The medical fluid delivery system of claim 3, wherein said fluid delivery set includes an actuation means mounted in a predetermined position on said fluid delivery set for detection by said sensor on said peristaltic pump for enabling operation of a rotor on said peristaltic pump.

5. A medical fluid delivery apparatus comprising a peristaltic pump having a first means thereon for moving fluid through a flexible tube on a fluid delivery set and a second means for preventing improper system operation, said second means including a switching component on said peristaltic pump in operative connection with and downstream of said first means, said switching component being switchable to a first sate in response to the detection of a predetermined alignment where a member on the delivery set which is properly spaced apart form said switching component on said peristaltic pump and said switching component is switchable to a second state when the delivery set is not properly spaced apart from said switching component on said peristaltic pump wherein operation of said first means is enabled in the first state and disabled in the second state of said switching component, wherein said predetermined alignment corresponds to a predetermined alignment of said conduit about said flow control member.

6. A fluid delivery apparatus comprising:

a motor set forming a housing for a fluid infusion device, a rotary fluid flow control member on said motor set, a switch for enabling the rotation of said fluid flow control, first and second receiving members on said motor set and said second receiving member being downstream of said fluid flow control means, a sensor adjacent said second receiving member and in communication with said switch for detecting the presence of a portion of a fluid delivery set operatively mounted adjacent said second receiving member, wherein said switch enables the operation of said fluid flow control member in response to the detection of a portion of the fluid delivery set by said sensor when said delivery set is in a predetermined alignment to enable the flow of a liquid through the fluid delivery set, wherein said predetermined alignment corresponds to a predetermined alignment of said conduit about said fluid flow control member.

7. The apparatus of claim 6, wherein said sensor is a magnetic field sensitive sensor for detecting the presence of a magnetic field source adjacent said second receiving member and spaced apart from said first receiving member on said portion of the fluid delivery set when the fluid delivery set is aligned in said predetermined alignment.

8. The apparatus of claim 6, wherein said fluid flow control member includes a rotationally operating rotor member thereon for the delivery of liquid to a patient at a controlled rate and wherein operation of said rotor member is enabled by said switch.

9. A medical fluid delivery system comprising:
a peristaltic pump having first and second receiving members and a rotatable rotor member thereon for the delivery of a medical fluid to a patient at a controlled rate;
a fluid delivery set including an upstream portion having a fluid reservoir section and a downstream portion having a fluid delivery section adapted to deliver fluid to a patient and a flexible tube section in fluid communication with said fluid reservoir section and said fluid delivery section, said flexible tube section operatively stretchable about at least a portion of said rotor member on said pump and including first and second mounting members spaced apart form each other and adapted to be inserted into said first and second recessed receivers;
said second mounting member being oriented downstream of said first mounting member;
a sensor on said peristaltic pump adjacent said second receiving member for detecting the placement of an activation means adjacent said second receiving member; and
said activation means operatively interposed between said second mounting member and said sensor to enable said pump to rotate said rotor member to deliver fluid to a patient when said source means is detected by said sensing means.

10. A disposable medical fluid delivery set adapted to be mounted on a separate fluid control apparatus in a predetermined and operation-activating alignment, the fluid delivery set comprising a conduit having aportion thereof which is stretchable for mounting about a portion of the fluid flow control apparatus and a sensed member operatively mounted downstream of said stretchable portion of said conduit wherein said sensed member is a magnetic field source and said sensed member is sensed by the flow control apparatus to enable the flow of a medical fluid to a patient through said conduit.

11. The fluid delivery set of claim 10 wherein said sensed member is sensed by a sensor on the fluid flow control apparatus when said stretchable portion of said conduit is properly stretched about a rotor on the fluid flow control apparatus thereby enabling the controlled flow of a medical fluid through said conduit.

12. The fluid delivery set of claim 10 wherein said sensed member is a magnetic field source.

13. The fluid delivery set of claim 10 wherein said sensed member forms part of a mounting member on said conduit and is positioned generally adjacent said stretchable portion of said conduit.

14. A disposable medical fluid delivery set dimensioned to be mounted on a separate fluid control apparatus in a predetermined and operation activating alignment, the fluid delivery set comprising a conduit having a compressible portion thereon and a magnetic field source mounted on said conduit and a drip chamber therein spaced apart form said magnetic field source to enable the controlled flow of a medical liquid to a patient therethrough.

15. The fluid delivery set of claim 14 wherein said compressible portion of said conduit is stretchable about a portion of the fluid control apparatus.

16. The fluid delivery set of claim 14 wherein said magnetic field source forms an abutment on said conduit which is sized to be received on the fluid control apparatus.

17. The fluid delivery set of claim 16 wherein a further abutment is formed on said conduit and said further abutment is sized to be received in a recess on the fluid control apparatus.

* * * * *

UNITED STATES PATENT AND TRADEMARK OFFICE
CERTIFICATE OF CORRECTION

PATENT NO.   :  6,017,326
DATED        :  January 25, 2000
INVENTOR(S)  :  Pasqualucci et al.

It is certified that error appears in the above-identified patent and that said Letters Patent is hereby corrected as shown below:

| | |
|---|---|
| Column 1, Line 12. | The word "enternal" is misspelled. Please change "enternal" to --enteral--. |
| Column 1, Line 19. | The word "enternal" is misspelled. Please change "enternal" to --enteral--. |
| Column 3, Line 50. | The number "9" is incorrect. Please change "9" to --19--. |
| Column 4, Line 28. | The word "seats" is misspelled. Please change "seats" to --sits--. |
| Column 5, Line 9. | The symbol "(c)" is misused. Please change "(c)" to --degrees--. |
| Claim 5 Line 44. | The word "form" is misspelled. Please change "form" to --from--. |
| Claim 9, Line 34. | The word "form" is misspelled. Please change "form" to --from--. |
| Claim 10, Line 6. | The word "aportion" is misspelled. Please change "aportion" to --a portion--. |
| Claim 14, Line 31. | The word "form" is misspelled. Please change "form" to --form--. |

Signed and Sealed this

Ninth Day of January, 2001

Attest:

Q. TODD DICKINSON

*Attesting Officer*     *Commissioner of Patents and Trademarks*